Figure 1:
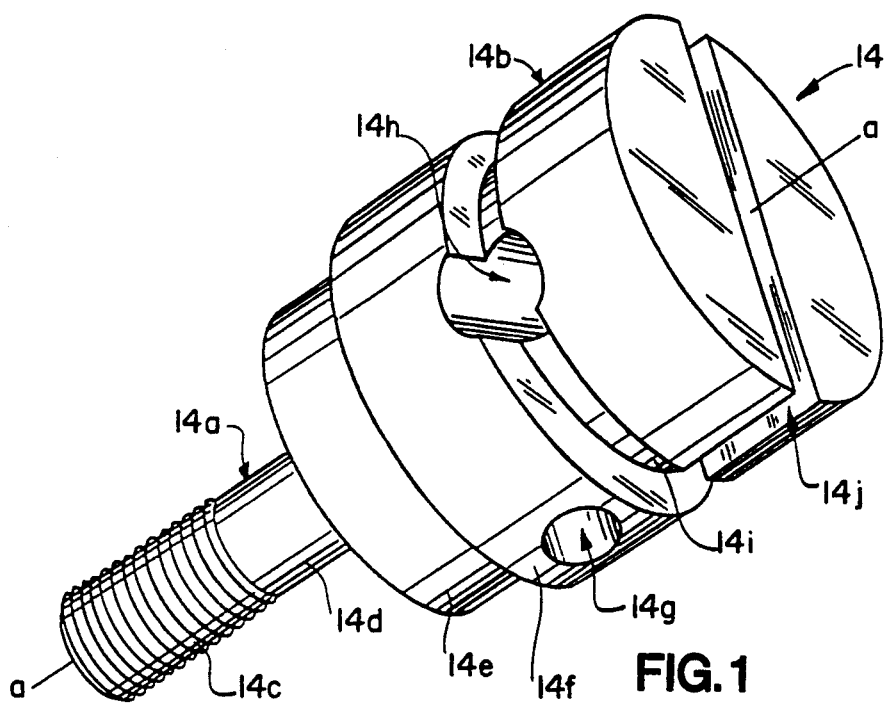

United States Patent [19]

Eckert

[11] Patent Number: 5,178,538
[45] Date of Patent: Jan. 12, 1993

[54] DENTAL PROPHYLACTIC CUP

[76] Inventor: Ronald C. Eckert, 4267 Sugar Maple La., Okemos, Mich. 48864

[21] Appl. No.: 608,340

[22] Filed: Nov. 2, 1990

[51] Int. Cl.⁵ .................................................. A61C 3/06
[52] U.S. Cl. ...................................... 433/166; 433/125
[58] Field of Search ............... 433/166, 125, 173, 174; 411/395, 422

[56] References Cited

U.S. PATENT DOCUMENTS

| | | | |
|---|---|---|---|
| 1,451,993 | 4/1923 | McLellan . | |
| 1,520,491 | 12/1924 | Weissleder | 433/216 |
| 1,620,990 | 3/1927 | Brothers | 433/216 |
| 1,644,465 | 10/1927 | Chott . | |
| 1,745,602 | 2/1930 | Chayes | 433/166 X |
| 1,809,907 | 6/1931 | Newcomb | 433/166 X |
| 1,837,938 | 12/1931 | Young . | |
| 2,093,006 | 9/1937 | Chott | 32/59 |
| 2,093,007 | 9/1937 | Chott | 433/216 |
| 2,105,618 | 1/1938 | Silva | 411/395 X |
| 2,135,933 | 11/1938 | Blair | 433/166 X |
| 2,168,000 | 8/1939 | Schuarte | 411/395 X |
| 3,091,033 | 5/1963 | Ellman | 32/58 |
| 3,599,333 | 8/1971 | Muhler | 433/166 |
| 3,789,462 | 2/1974 | Riech | 32/59 |
| 3,977,083 | 8/1976 | Leslie et al. | 32/58 |
| 3,977,084 | 8/1976 | Sloan | 32/59 |
| 3,985,147 | 10/1976 | Ricketts et al. | 132/89 |
| 4,011,602 | 3/1977 | Rybicki et al. | 433/173 X |
| 4,097,995 | 7/1978 | Danne et al. | 32/58 |
| 4,177,562 | 12/1979 | Miller et al. | 433/174 |
| 4,259,071 | 3/1981 | Warden et al. | 433/166 |
| 4,266,933 | 5/1981 | Warden et al. | 433/82 |
| 4,335,731 | 6/1982 | Bora, Jr. | 433/216 |
| 4,365,956 | 12/1982 | Bailey | 433/125 X |
| 4,381,792 | 5/1983 | Busch, Jr. et al. | 433/216 |
| 4,447,208 | 5/1984 | Kawai | 433/166 |
| 4,539,874 | 9/1985 | Jacovitz | 411/403 X |
| 4,601,661 | 7/1986 | Du Be et al. | 433/134 |
| 4,636,171 | 1/1987 | Martin | 433/134 |
| 4,754,749 | 7/1988 | Tsou | 411/403 X |
| 4,960,381 | 10/1990 | Niznick | 433/173 X |
| 5,030,095 | 7/1991 | Niznick | 433/173 |
| 5,080,542 | 1/1992 | Sheahan | 411/395 X |

Primary Examiner—Cary E. O'Connoir
Assistant Examiner—Nicholas D. Lucchesi
Attorney, Agent, or Firm—Ian C. McLeod

[57] ABSTRACT

An improved prophylactic cup device (10, 100) comprised of a prophylactic cup (12, 102) mounted on a mounting screw (14, 104) is described. In the preferred embodiment, the prophylactic cup is molded from a silicone polymer containing a dental cleaning and polishing agent such as pumice and is mounted onto a circular cross-sectioned mounting screw comprised of a shaft (14a) with a threaded portion (14c) and a head (14b). The head provides for cylindrical inlet or channel portions (14g) and (14h), and retaining slots (14i) and (14j). Since silicone polymers are poorly adherent to any surface and because the strength of silicone polymers is greatly reduced by the addition of pumice, the channels and retaining slots increase the contact surface area between the prophylactic cup and the mounting screw. This allows the prophylactic cup device to be mounted on a dental handpiece and to be used to clean teeth and gingival crevices without a dental paste. A prophylactic cup device (110) and a dental handpiece (112) comprising a disposable unit are also shown.

36 Claims, 3 Drawing Sheets

DENTAL PROPHYLACTIC CUP

BACKGROUND OF THE INVENTION (1) Field of the Invention

The present invention relates to an improved flexible prophylactic cup particularly adapted for mounting onto a dental hand tool. In particular, the present invention relates to a screw assembly with an inletted head for mounting a molded prophylactic cup onto a dental hand tool and the shape of the working surface of the cup. The prophylactic cup is preferably molded from a silicone polymer, usually containing a dental cleaning and polishing agent such as pumice, uniformly dispersed throughout the polymer. Silicone polymers are poorly adherent to any surface. Therefore, when pumice is added to the silicone polymer, the strength of the silicone polymer is reduced. This strength reduction is often manifested at the point where the cup is molded to a mounting screw or mandrel. Because of the reduced strength, the torque stress causes the cup to become loose and separate from the mounting screw before the teeth cleaning procedure is completed. The present invention preferably overcomes these inherent drawbacks by providing a number of interconnected inlet portions comprised of channels and grooves through the head of the mounting screw. This greatly increases the bonding surface and the bonding strength between the molded silicone polymer and the mounting screw and provides for the bonding to be achieved by mechanical retention.

(2) Prior Art

The prior art has described various types of dental instruments for cleaning stains and plaque from teeth and gingival crevices Some of the prior art devices use a prophylactic cup or a polishing cup mounted on a dental handpiece. Prophylactic cup paste is usually repeatedly applied to the cup in use. The polishing cup can be supplied with a dental cleaning paste that is contained in the dental handpiece and pumped through a channel in the polishing cup to the teeth. U.S. Pat. Nos. 3,977,083 to Leslie et al and 3,977,084 to Sloan shows this type of device. The dental handpieces in these devices are not disposable as in the present invention and must be sterilized between patients.

U.S. Pat. No. 3,789,462 to Riech shows a prophylactic cup that is formed from an elastomeric urethane polymer filled with pumice or other abrasive agents. This device does not require a dental paste because the abrasive pumice is evenly dispensed throughout the elastomeric material. The polyurethane polymer bonds well to the screw; however, this device is used at the expense of the health and safety of the patient because of the toxic nature of urethane materials. Also the shape of the cup is not optimal for cleaning teeth.

The prior art has also shown rotatable disks with embedded abrasive material, rotatable brushes that require an abrasive to be added to the brushes and various shapes of rigid tools that are used for dental hygiene. Illustrative of these prior art devices are U.S. Pat. Nos. 1,451,993 to McLellan; 1,520,491 to Weissleder; 1,620,990 to Brothers; 2,093,007 to Chott; 3,091,033 to Ellman; 3,985,147 to Ricketts et al; 4,335,731 to Bora, Jr.; 4,381,792 to Busch, Jr. et al and 4,601,661 to Du Bé et al.

OBJECTS

It is therefore an object of the present invention to provide an improved dental prophylactic cup formed of a non-toxic polymer impregnated with an abrasive that will not separate from a mounting screw or other holder member when the prophylactic cup is mounted into a dental hand tool and used to clean teeth. Further, it is an object of the present invention to provide a prophylactic cup formed of a non-toxic, abrasive impregnated polymer with a novel inletted mounting screw so that the cup can be mounted onto a dental hand tool for cleaning teeth. Further, it is an object of the present invention to provide a novel mounting screw for mounting a prophylactic cup onto a dental hand tool wherein a head of the mounting screw provides a unique interconnection of inletted portions providing a bonding surface such that the cup will not separate from the mounting screw when angular momentum is imparted to the cup by the dental hand tool. Still further, it is an object of the present invention to provide an improved dental prophylactic cup mounted onto a disposable dental hand tool that is relatively simple and inexpensive to manufacture. These and other objects will become increasingly apparent by reference to the following descriptions and to the drawings.

IN THE DRAWINGS

FIG. 1 is a perspective view of a circular cross-sectioned mounting screw 14 comprising a shaft 14a with a threaded portion 14c and a head 14b with inlet portions or channels 14g and 14h, and retaining slots 14i and 14j.

Figure 2:
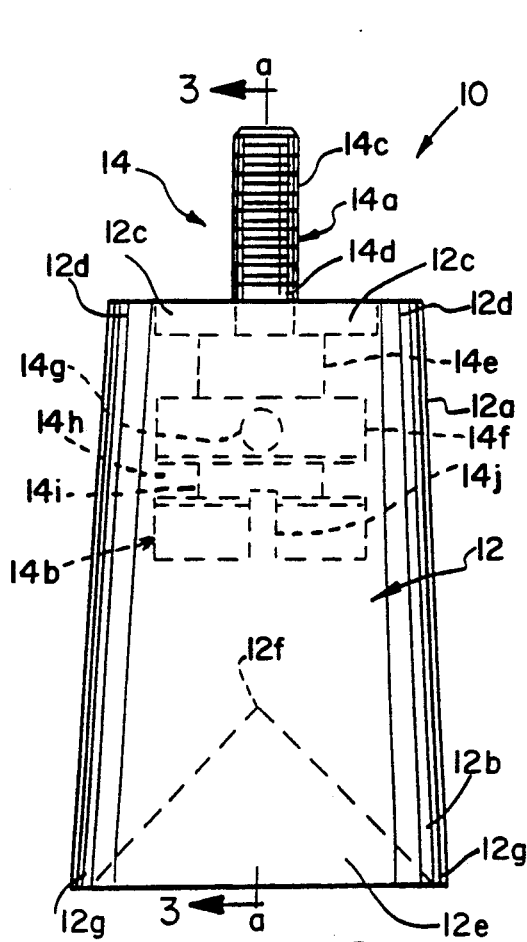

FIG. 2 is a front cross-sectioned view of a prophylactic cup device 10 comprised of a prophylactic cup 12 mounted on the mounting screw 14.

Figure 3:
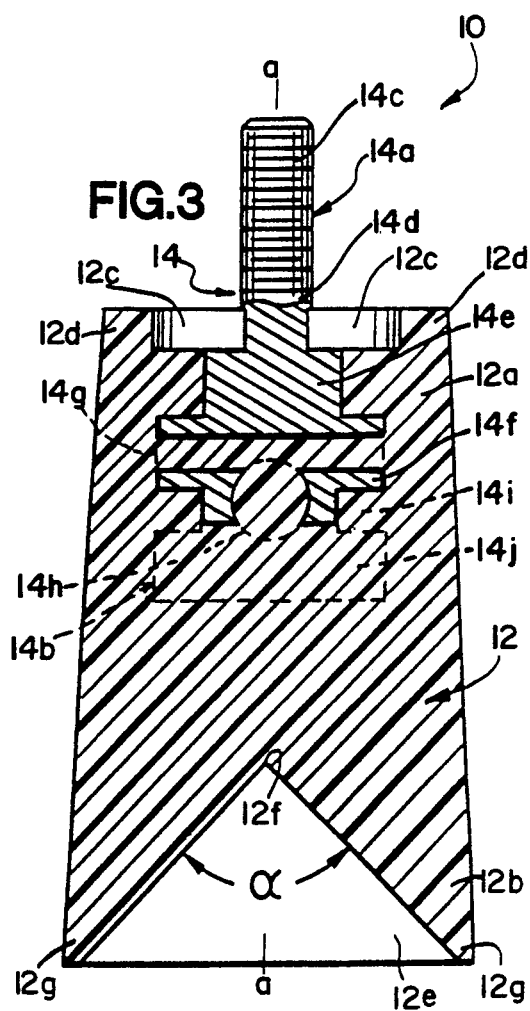

FIG. 3 is a front cross-sectioned view along line 3—3 of FIG. 2 showing the prophylactic cup 12 molded on the mounting screw 14 and interlocked with the inlet portions or channels 14g and 14h and the retaining slot 14i.

Figure 4:
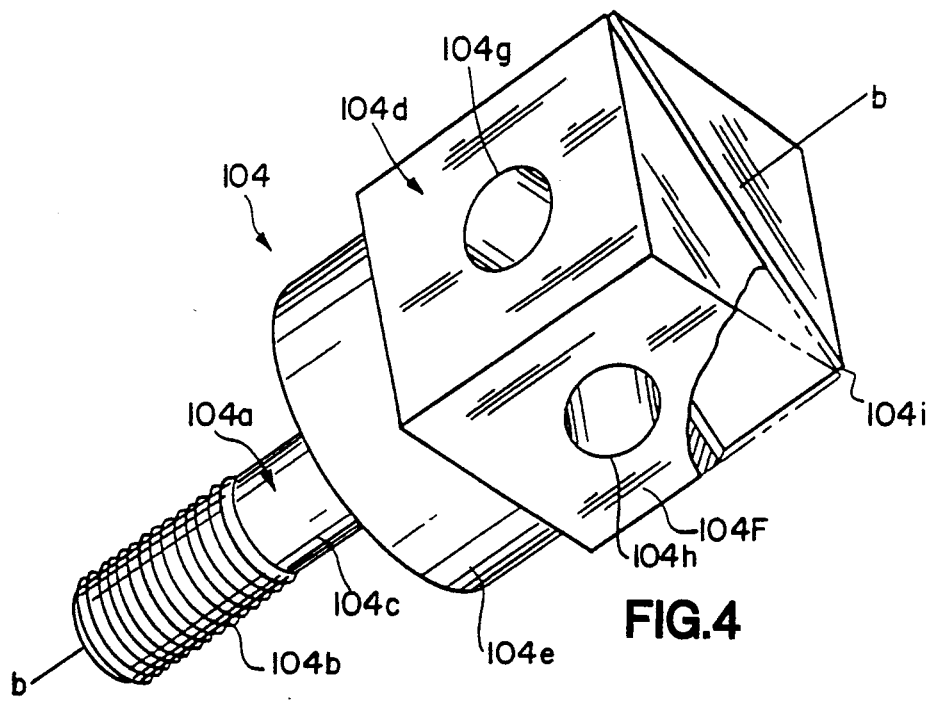

FIG. 4 is a perspective view of a mounting screw 104 comprised of a circular cross-sectioned shaft 104a with threaded portion 104b and a head 104d having a square cross-sectioned enlarged portion with inlet portions or channels 104g and 104h and a retaining slot 104i.

Figures 5, 6:
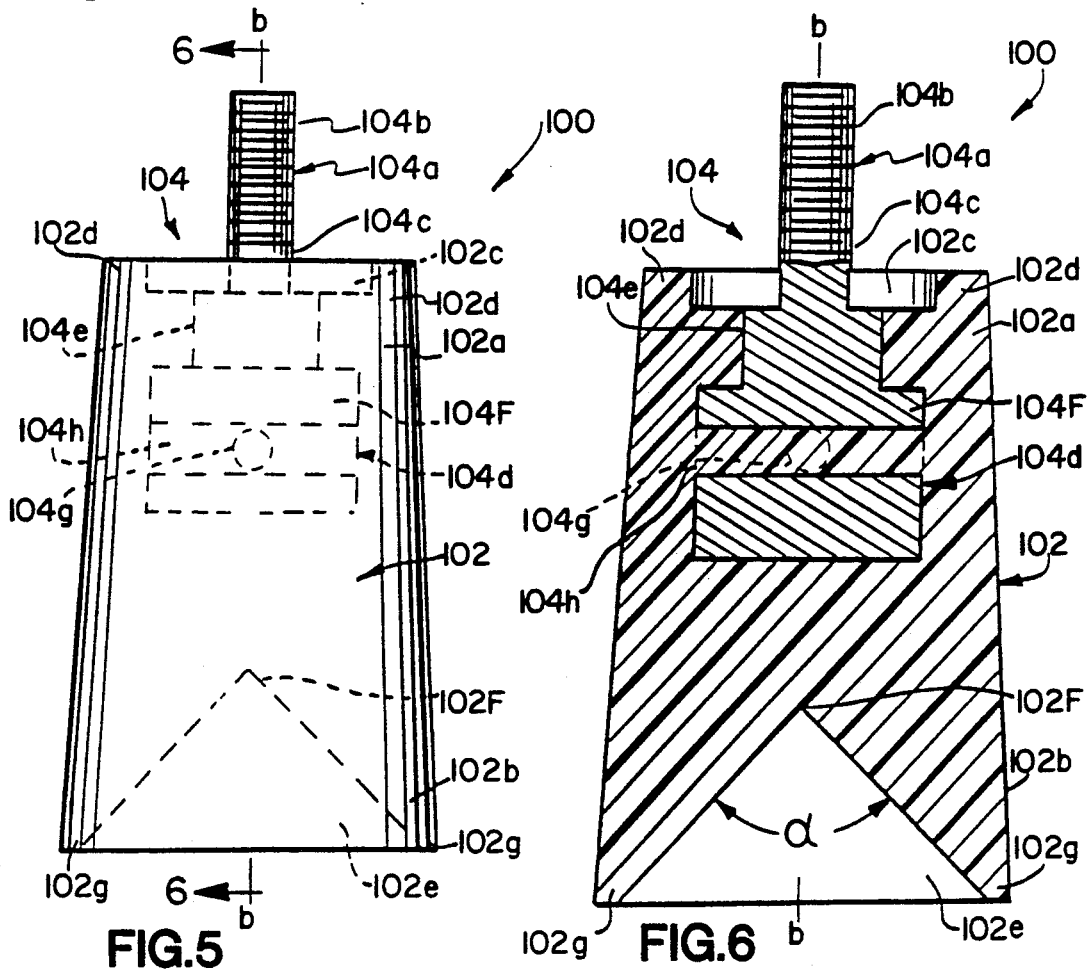

FIG. 5 is a front cross-sectioned view of a prophylactic cup device 100 comprised of a prophylactic cup 102 mounted on the mounting screw 104.

FIG. 6 is a front cross-sectioned view along line 6—6 of FIG. 5 showing the prophylactic cup 102 molded on the mounting screw 104 and interlocked with the inlet portions or channels 104g and 104h.

Figure 7:
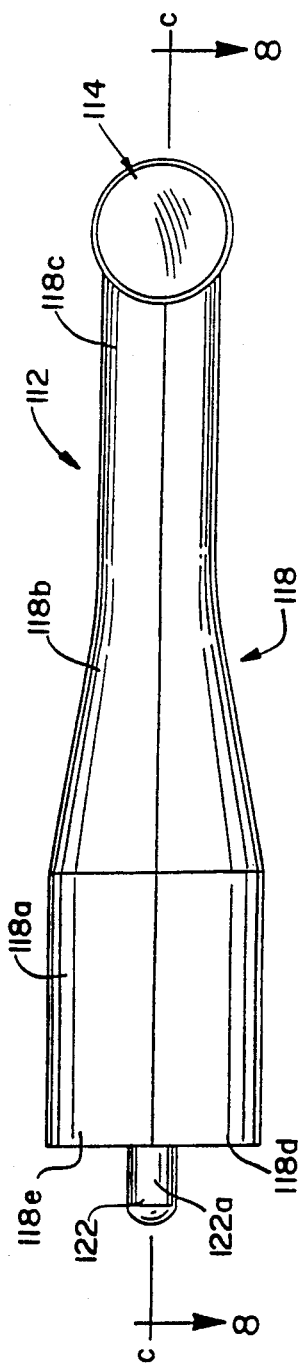

FIG. 7 is a bottom plan perspective view of dental handpiece 112 and a prophylactic cup 114 mounted on the dental handpiece 112.

Figure 8:
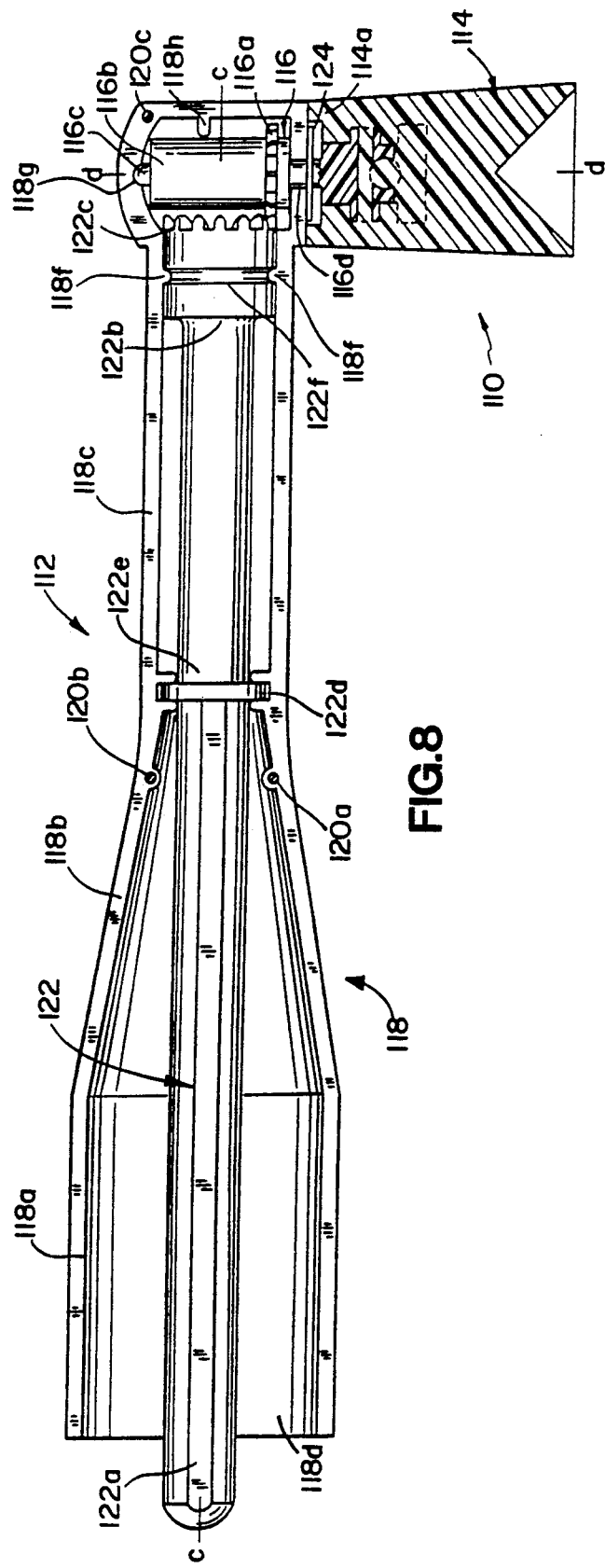

FIG. 8 is a front cross-sectional view along line 8—8 of FIG. 7 showing a primary drive shaft 122 mounted in the dental handpiece 112 with a prophylactic cup 114 molded onto a unitary mounting screw and gear drive shaft 116 mounted in the dental handpiece 112 and connected to the drive shaft 122.

GENERAL DESCRIPTION

The present invention relates to a flexible prophylactic cup for cleaning teeth comprised of an elastomeric material mounted on a holding member, the improvement in the holding member which comprises: a holding portion having a longitudinal axis and having a proximal end which is rotated by a rotating means on a dental handpiece and having a distal end; and a head portion mounted on the distal end of the holding portion along the axis with one end having a shoulder mounted adjacent to the handpiece and an opposed end along the axis, wherein the head portion is provided with an inletted portion intermediate the ends and wherein the cup is mounted on the head portion with the material filled in the inletted portion such that the cup remains on the head portion as teeth are cleaned with the cup.

The present invention also relates to a flexible prophylactic cup comprised of an elastomeric material mounted on a holding member, the improvement in the holding member which comprises: a holding portion having a longitudinal axis and having a proximal end which is rotated by a rotating means on a dental handpiece and having a distal end; and a head portion mounted on the distal end of the holding portion along the axis with one end having a shoulder mounted adjacent to the handpiece and an opposed end along the axis, wherein the head portion is provided with at least two holes through the head portion which are across the axis and wherein the opposed end of the head portion has at least one slot across the opposed end and wherein the cup is mounted on the head portion with the material filled in the holes and slot, which are preferably interconnected.

Further, the present invention relates to a threaded member for a flexible prophylactic cup comprised of an elastomeric material mounted over the threaded member which removably mounts on a dental handpiece for cleaning teeth, the improvement which comprises: a threaded portion around and along a longitudinal axis of the threaded portion having a proximal end which threads into a rotating member on the handpiece and a distal end; and a head portion provided on the distal end of the threaded portion along the axis with one end having a shoulder mounted adjacent to the rotating member of the handpiece and an opposed end along the axis, wherein the head portion is provided with at least two holes through the head portion which are across the axis and wherein the opposed end of the head portion has at least one slot across the opposed end and wherein the cup can be mounted on the head portion with the material in the holes and slot.

The polymer material is preferably a silicone polymer. Medical grade silicone polymer manufactured by Dow Corning, Inc., Midland, Mich. is most preferred. This polymer is catalyzed with platinum rather than hydrogen peroxide which is used for most commercial applications. Platinum is used where the silicone is to be used in medical applications. Other polymers are known and can be used if they are suitable for use in the mouth or for laboratory purposes. The polymer material preferably contains between 20 and 50 percent by weight of the abrasive material. The abrasive material for dental purposes can be pumice or pumice based powders; quartz and quartz based powders, zirconium silicate and zirconium silicate based powders and feldspar and feldspar based powders as specified by ANSI/ADA Specification to 37-1986. Type I up to 150 microns is for oral use and Type II up to 250 microns is for laboratory use such as on false teeth.

The polymer material can be filled with medicament compounds such as sodium fluoride anti-caries agent or strontium chloride which is a teeth desensitizer.

As used herein the term "cleaning" includes polishing, rubbing and the like. The term "cleaning" is used in its most genuine sense. The cup can have a cone angle (alpha in FIGS. 3 and 6) of between about 75° and 142°. An angle of 93° is preferred.

The holding member or mounting screw can be made in a molding process with release pins in the mold for forming the inletted portions. The inletted portions and grooves could also be drilled or cut into the mounting screw after the main body of the screw has been formed by a molding or drilling process.

The prophylactic cup can be molded onto a threaded mounting screw for threadedly mating with the dental handpiece or the prophylactic cup can be molded onto the mounting screw which is then assembled into a dental handpiece as a disposable unit. Another embodiment of the present invention which is presently in use has a latch-type mechanical connection between the holding member and the dental handpiece. In the latch-type embodiment, the holding member has a groove formed in a shaft at the end of the holding member, opposite the prophylactic cup. When the holding member is inserted into the dental handpiece, a releasable latch in the handpiece snaps into the groove and secures the prophylactic cup onto the dental handpiece. To release the prophylactic cup, a release button on the dental handpiece is pushed. This retracts the retractable latch and releases the prophylactic cup and holding member in a quick-release manner.

SPECIFIC DESCRIPTION

FIGS. 1 to 3 show a preferred embodiment of a prophylactic cup device 10 comprised of a prophylactic cup 12 mounted on a preferred mounting screw 14 for securing the prophylactic cup 12 onto a dental handpiece. The mounting screw 14 comprises a shaft 14a and a head 14b. The shaft 14a has a circular cross-section along the axis a—a and comprises a threaded portion 14c and an unthreaded portion 14d. As shown in FIG. 1, the threaded portion 14c is larger in cross-section along the axis a—a than the unthreaded portion 14d. The head 14b extends from the unthreaded portion 14d of the shaft 14a and also has a circular cross-section along the axis a—a. The head 14b comprises a proximal cylindrical portion 14e and a distal enlarged cylindrical portion 14f extending from the proximal cylindrical portion 14e opposite the shaft 14a.

As shown in FIGS. 1 to 3, the enlarged portion 14f has interconnecting first and second inlet portions or channels 14g and 14h and a first retaining slot 14i and a second retaining slot 14j. The channels 14g and 14h are spaced 90° apart and are cylindrical with a circular cross-section along their axis perpendicular to the axis a—a. The channels 14g and 14h also interconnect at the point where they intersect the axis a—a (FIG. 3). When the prophylactic cup 12 is molded around the mounting screw 14, the interconnection between the channels 14g and 14h and slot 14i helps to strengthen the interlock between the prophylactic cup 12 and the screw 14.

The first slot 14i extends radially around the axis a—a and intersects the second channel 14h at the opposed ends of the channel 14h (FIG. 2). The second slot 14j is provided in the enlarged section 14f opposite the cylindrical section 14e of the head 14b. The second slot 14j extends through the enlarged section 14f to a depth sufficient to partially intersect the second channel 14h (FIG. 3) and to interconnect with the first slot 14i. The second slot 14j has a rectangular cross-section along an axis perpendicular to the axis a—a and partially intersects the second channel 14h (FIG. 3) at a right angle to the axis of the channel 14h. The retaining slots 14i and 14j in conjunction with the channels 14g and 14h, also add strength to the interlock between the prophylactic cup 12 and the mounting screw 14 by increasing the contact surface area between the cup 12 and the screw 14.

The prophylactic cup 12 is a molded member formed in a frusto-conical shape that encases the head 14b of the mounting screw 14, having a proximal end 12a and a distal end 12b. The frusto-conical shape of the prophylactic cup 12 tapers inwardly towards the axis a—a from the distal end 12b to the proximal end 12a. The proximal end 12a of the cup 12 has an annular recess 12c around the axis a—a and the unthreaded portion 14d of the shaft 14a, adjacent to the cylindrical portion 14e of the head 14b of the mounting screw 14. The annular recess 12c forms a shoulder 12d at the proximal end 12a of the cup 12 which is mounted against a rotating member of a dental handpiece (not shown).

The distal end 12b of the prophylactic cup provides for a conical recess 12e that tapers inwardly from the distal end 12b towards the axis a—a and the proximal end 12a of the cup 12. An apex 12f of the cone 12e is on the axis a—a, spaced from the head 14b of the screw 14.

The distal end 12b of the cup 12 is radially larger than the base of the cone 12e thereby forming a shoulder 12g at the distal end 12b of the cup 12. The shoulder 12g gives the cup 12 increased strength at the functional or distal end 12b and allows the cone 12e to be used either with or without a dental cleaning paste (not shown) for cleaning teeth and gingival crevices when the prophylactic cup device 10 is rotatably mounted onto a dental handpiece (not shown).

Another embodiment of a prophylactic cup device 100 comprised of a prophylactic cup 102 molded onto a mounting screw 104 for mounting the prophylactic cup 102 onto a dental handpiece is shown in FIGS. 4 to 6. The mounting screw 104 has a shaft 104a comprised of a threaded portion 104b and an unthreaded portion 104c, and a head 104d comprised of a proximal cylindrical portion 104e and a distal enlarged cylindrical portion 104f extending from the proximal cylindrical portion 104e opposite the shaft 104a. The mounting screw 104 is similar to the mounting screw 14 (FIG. 1 to 3) except that the enlarged portion 104f has a square cross-section along the axis b—b.

As shown in FIGS. 4 to 6, the enlarged portion 104f of the mounting screw 104 provides for interconnecting first and second inlet portions or channels 104g and 104h, and a retaining slot 104i. The channels 104g and 104h are spaced 90° apart and are cylindrical with a circular cross-section along the axis b—b. The channels 104g and 104h also interconnect at the point where their respective axis intersect the axis b—b. The retaining slot 104i is provided diagonally across the enlarged section 104f to a depth sufficient to intersect with the channels 104g and 104h. This helps to strengthen the interlock between the prophylactic cup 102 and the mounting screw 104.

Similar to the prophylactic cup 12 in FIGS. 1 to 3, the prophylactic cup 102 in FIG. 4 to 6 is a molded member formed in a frusto-conical shape that encases the head 104d of the mounting screw 104, having a proximal end 102a and a distal end 102b. The frusto-conical shape of the prophylactic cup 102 tapers inwardly towards the axis b—b from the distal end 102b to the proximal end 102a. The proximal end 102a of the cup 102 has an annular recess 102c around the axis b—b and the unthreaded portion 104c of the shaft 104a, adjacent to the cylindrical portion 104e of the head 104d of the mounting screw 104. The annular recess 102c forms a shoulder 102d at the proximal end 102a of the cup 102 which is mounted against a rotating member of a dental handpiece (not shown).

The distal end 102b of the prophylactic cup 102 provides for a cone shaped recess 102e that tapers inwardly from the distal end 102b towards the axis b—b and the proximal end 102a of the cup 102. An apex 102f of the cone 102e is on the axis b—b spaced from the head 104d of the screw 104. The distal end 102b of the cup 102 is radially larger than the base of the cone 102e thereby forming a shoulder 102g at the distal end 102b of the cup 102. The shoulder 102g gives the cup 102 increased strength at the functional or distal end 102b and allows the cone 102e to be used either with or without a dental cleaning paste (not shown) for cleaning teeth and gingival crevices similarly to the prophylactic cup 12 in FIGS. 1 to 3.

FIG. 8 shows a preferred disposable dental handpiece 112. A prophylactic cup device 110 and the dental handpiece 112 comprises a disposable unit that is discarded after it is used to clean the teeth of a patient. The prophylactic cup device 110 is comprised of a prophylactic cup 114 and a unitary mounting screw and gear drive shaft 116. The prophylactic cup 114 is similar to the prophylactic cups 12 and 102. The dental handpiece 112 comprises an elongated main body 118 which has a circular cross-section along the axis c—c with an enlarged proximal end 118a for holding by a dentist or hygienist, a tapered intermediate section 118b and a distal end 118c. As shown in FIG. 7, the dental handpiece 112 is molded with a right half 118d and a left half 118e that are glued together with pin projections (not shown) on the left half 118e mating with recesses 120a, 120b and 120c in the right half 118d (FIG. 8).

As shown in FIG. 8, the inside of the dental handpiece 112 halves 118d and 118e are hollowed and provide for a primary drive shaft 122, and the unitary mounting screw and geared drive shaft 116. The primary drive shaft 122 has a proximal end 122a that attaches to a conventional electric motor in a dental handpiece (not shown) for providing a torque to the shaft 122 and a distal end 122b provided with a cogwheel 122c. An annular governor ring 122d, provided at an intermediate position 122e on the primary drive shaft 122, helps to reduce wobble in the shaft 122 and helps to keep the shaft 122 rotating on the axis c—c. Adjacent to the cogwheels 122c at the distal end 122b of the primary drive shaft 122 is an annular groove 122f. The annular groove 122f mates with an annular tab portion 118f on the right and left halves 118d and 118e of the main body 118 of the dental handpiece 112 (only the right half 118d shown) and also helps to stabilize the journaled rotation of the primary drive shaft 122 on the axis c—c.

The cogwheel 122c at the distal end 122b of the primary drive shaft 122 meshes with a gear wheel 116a on the shaft 116. The gear wheel 116a changes the direction of the torque of the shaft 122 to the axis d—d which is perpendicular to the axis c—c. The proximal end 116b of the shaft 116 has an annular locating tab 116c along the axis d—d that is mounted in a locating recess 118g in the right and left halves 118d and 118e of the main body 118 of the dental handpiece 112 (only the right half 118d shown). A stabilizing tab 118h in the right and left halves 118d and 118e also helps to maintain the rotation of the shaft 116 along the axis d—d. An annular washer 124 is positioned around an unthreaded portion 116d of the shaft 116 adjacent to a shoulder 114a of the prophylactic cup 114 and helps to stabilize the rotation of the cup 114 on the axis d—d.

IN OPERATION

In operation, the prophylactic cup device 10 in FIGS. 2 and 3 and the prophylactic cup device 100 in FIGS. 5 and 6 are threadedly mounted onto a disposable dental handpiece. Since the prophylactic cup 12 and 102 are molded from a silicone material with pumice impregnated throughout, there is no need to apply a prophylactic paste in association with the cups 12 and 102. After a dentist or hygienist has thoroughly cleaned the teeth and gingival crevices of plaque and stains, the cup device 10 or 104 is disposed of or the entire dental handpiece 112 with the prophylactic cup device 10 is disposed of as a unit. This greatly enhances the infection control and reduces the risk of pathogenic organisms being passed from one patient to another and also saves the time that would normally be required to sterilize a handpiece. The conical recess in the distal end of the cup is uniquely shaped to provide maximal contact of the flexible silicone polymer with the tooth surface. In use the working surface wears down providing continuous application of fresh abrasive to the tooth surface.

It is intended that the foregoing descriptions only be illustrative of the present invention and the invention is limited only by the hereinafter appended claims.

I claim:

1. In a flexible prophylactic cup for cleaning teeth comprised of an elastomeric material mounted on a holding member, the improvement in the holding member, which comprises:
   (a) a holding portion having a longitudinal axis and having a proximal end which is rotated by a rotating means on a dental handpiece and having a distal end; and
   (b) a head portion mounted on the distal end of the holding portion along the longitudinal axis with one end of the head portion mounted adjacent to the handpiece and an opposed end along the longitudinal axis, wherein the head portion is provided with an inlet portion that extends through the head portion intermediate the ends of the head portion and wherein the cup is mounted on the head portion with the material filled in the inlet portion to lock the prophylactic cup on the head portion of the holding member so that the cup remains on the head portion as the teeth are cleaned with the cup.

2. In a flexible prophylactic cup comprised of an elastomeric material mounted on a holding member, the improvement in the holding member, which comprises:
   (a) a holding portion having a longitudinal axis and having a proximal end which is rotated by a rotating means on a dental handpiece and having a distal end; and
   (b) a head portion mounted on the distal end of the holding portion along the longitudinal axis with one end of the head portion having a shoulder mounted adjacent to the handpiece and an opposed end along the axis, wherein the head portion is provided with at least two holes through the head portion which are across the axis and wherein the opposed end of the head portion has at least one slot across the opposed end and wherein the cup is mounted on the head portion with the elastomeric material filled in the holes and the slot.

3. The cup of claim 2 wherein the holding portion is part of a disposable attachment for the dental handpiece with mating angle gears and a housing supporting the holding portion and gears and wherein one of the gears is provided towards the proximal end of the holding portion of the holding member.

4. The attachment of claim 3 wherein the gears, housing and holding member are comprised of a plastic material.

5. In a flexible prophylactic cup comprised of an elastomeric material mounted over a threaded member, which removeably mounts on a dental handpiece for cleaning teeth, the improvement in the threaded member defined, which comprises:
   (a) a threaded portion around and along a longitudinal axis of the threaded member having a proximal end which threads into a rotating member on the handpiece and a distal end; and
   (b) a head portion provided on the distal end of the threaded member along the axis with one end of the head portion having a shoulder mounted adjacent to the rotating member of the handpiece and an opposed end along the axis, wherein the head portion is provided with at least two holes through the head portion which are across the axis and wherein the opposed end of the head portion has at least one slot across the opposed end and wherein the cup is mounted on the head portion with the material in the holes and the slot.

6. The cup of claim 5 wherein the threaded member has two holes that are spaced 90° from each other around the axis and wherein the two holes intersect.

7. The cup of claim 6 wherein the slot intersects one of the holes along the axis.

8. The cup of claim 7 wherein the slot is parallel to one of the holes.

9. The cup of claim 5 wherein the cup is composed of a silicone polymer as the material.

10. The cup of claim 9 wherein the silicone polymer is filled with a finely divided abrasive having a particle size between about 10 and 250 microns.

11. The cup of claim 10 wherein the silicone polymer contains between about 20 and 50 percent by weight abrasive.

12. The cup of claim 11 wherein the abrasive is pumice.

13. The cup of claim 5 wherein the cup has an opening in the shape of a cone with an apex angle between about 75° and 142° so that the cup can be used without a dental paste for polishing teeth.

14. The cup of claim 5 wherein the head portion of the threaded member has a circular cross-section perpendicular to the axis and a radial groove around the head portion perpendicular to the axis which intersects one of the holes.

15. The cup of claim 5 wherein the head portion of the threaded member has a square cross-section perpendicular to the axis.

16. A threaded member for mounting a flexible prophylactic cup on a dental handpiece for cleaning teeth, the improvement in the threaded member, which comprises:
   (a) a threaded portion around and along a longitudinal axis of the threaded member having a proximal end that removeably threads into a rotating member on the handpiece and a distal end; and
   (b) a head portion having a circular cross-section perpendicular to the longitudinal axis provided on the distal end of the threaded member and having an outside sidewall along and around the longitudinal axis with one end of the head portion having a shoulder mounted adjacent to the rotating member of the handpiece and an opposed end along the longitudinal axis, wherein the head portion is provided with at least two intersecting openings with a circular cross-section that extend through the head portion and across the longitudinal axis and wherein each of the openings has spaced apart open ends on opposed portions of the outside sidewall of the head portion to provide an opening through the head portion, wherein the opposed end of the head portion has at least one slot across the opposed end, wherein a radial groove is provided around the head portion, perpendicular to the longitudinal axis with the groove intersecting at least one of the open ends of one of the openings extending through the outside sidewall of the head portion, and wherein the prophylactic cup is comprised of an elastomeric material that can be mounted on the head portion with the elastomeric material filled in the openings and the slot to form an integral interlock of the prophylactic cup on the head portion of the threaded member.

17. The threaded member of claim 16 wherein two openings in the head portion are spaced 90° from each other around the longitudinal axis.

18. The threaded member of claim 16 wherein the slot intersects one of the openings along the longitudinal axis.

19. The threaded member of claim 16 wherein the slot is parallel to one of the openings.

20. A method for producing a prophylactic cup, which comprises:
(a) providing a holding member having a longitudinal axis with a holding portion of the holding member having a proximal end, which is rotated by a rotating means on a dental handpiece, and a distal end; and
(b) molding the prophylactic cup on a head portion of the holding member mounted on the distal end of the holding portion, opposite the proximal end, wherein the head portion has an outside sidewall along and around the longitudinal axis, with at least two holes providing openings that extend through the outside sidewall of the head portion across the longitudinal axis, wherein the holes have spaced apart ends on opposed portions of the outside sidewall of the head portion, wherein a radial groove is provided around the head portion, perpendicular to the longitudinal axis with the groove intersecting at least one of the open ends of one hole extending through the outside sidewall of the head portion, and wherein when the prophylactic cup is molded on the head portion, a portion of the prophylactic cup is filled in the holes in the head portion and groove to form an integral interlock of the prophylactic cup on the head portion of the holding member.

21. The method of claim 20 wherein the cup is molded of a silicone polymer as the material.

22. The method of claim 21 wherein the silicone polymer is filled with a finely divided abrasive having a particle size between about 10 and 250 microns so that the cup can be used without a dental paste for polishing teeth.

23. The method of claim 22 wherein the silicone polymer contains between about 20 and 50 percent by weight abrasive.

24. The method of claim 23 wherein the abrasive is pumice.

25. The method of claim 20 wherein the prophylactic cup has a proximal end and a distal end with a circular cross-sectioned outside sidewall along the longitudinal axis and between the ends and wherein the prophylactic cup has a molded opening in the shape of a cone with a base of the cone opening at the distal end of the cup having a first diameter smaller than the diameter of the distal end of the cup to thus form an annular shoulder at the distal end of the prophylactic cup, and wherein an apex angle of the cone opening is between about 75° and 142° so that the cup can be used without a dental paste for polishing teeth.

26. The method of claim 20 wherein the head portion of the threaded member has a square cross-section perpendicular to the axis.

27. A screw assembly for mounting a prophylactic cup on a dental handpiece, comprising:
(a) a shaft means having a cylindrical cross-section along a longitudinal axis with opposed ends wherein one of the ends is threaded for threadingly mounting the prophylactic cup on the dental handpiece and wherein the other end is unthreaded; and
(b) a head means extending from the unthreaded end of the shaft means, the head means having spaced apart ends and an outside sidewall along the longitudinal axis wherein one end of the head means is adjacent to the unthreaded end of the shaft means and the other end of the head means provides an enlarged section that extends from the one end of the head means, opposite the shaft means and wherein there are at least two intersecting holes across the axis providing channels through the head means, intermediate the spaced apart ends with the holes having spaced apart open ends provided on opposed portions of the outside sidewall of the head means, wherein there is at least one groove in the enlarged section of the head means, wherein the prophylactic cup has a shaped body molded from a resilient, abrasive, elastomeric material containing a dental cleaning and polishing agent uniformly dispersed therein and the head means serves for mounting the prophylactic cup on the screw assembly with the elastomeric material enveloping the head means and filling the holes in the head means to form an integral interlock of the prophylactic cup on the head means of the screw assembly.

28. The screw assembly of claim 27 wherein the channels are at right angles to each other and wherein a plane through the longitudinal axis of the shaft means bisects the channels.

29. The screw assembly of claim 27 wherein the enlarged section of the head means is provided with a first groove across the other end of the head means and has a circular cross-section along the longitudinal axis and wherein a second radial groove in the enlarged section has a second axis that is coaxial with the longitudinal axis of the shaft means with the second groove intersecting one of the channels at opposed ends of the channel.

30. The screw assembly of claim 27 wherein the enlarged section of the head means has a rectangular cross-section along an axis corresponding to the axis of the shaft means and wherein there is a groove in the enlarged section.

31. The screw assembly of claim 30 wherein the groove is diagonally across the rectangular cross-section of the enlarged section.

32. A method for cleaning teeth, which comprises:
  (a) providing a flexible prophylactic cup comprised of an elastomeric material mounted over a holding member, the improvement in the holding member defined, which comprises: a holding portion having a longitudinal axis and having a proximal end which is rotated by a rotating means on a dental handpiece and a distal end; and a head portion provided on the distal end of the holding portion along the longitudinal axis with one end of the head portion having a shoulder mounted adjacent to the handpiece and an opposed end along the axis, wherein the head portion is provided with at least two holes through the head portion which are across the axis and wherein the opposed end of the head portion has at least one slot across the opposed end and wherein the cup is mounted on the head portion with the material in the holes and the slot; and
  (b) cleaning the teeth with the prophylactic cup whole holding the dental handpiece.

33. The method of claim 32 wherein the cup is composed of a silicone polymer as the material filled with a finely divided abrasive having a particle size between about 10 and 250 microns and wherein the cup has an opening in the shape of a cone with an angle between about 75° and 142° so that the cup polishes the teeth.

34. The method of claim 33 wherein the silicone polymer contains between about 20 and 50 percent by weight abrasive.

35. The method of claim 34 wherein the abrasive is pumice.

36. A method for producing a prophylactic cup, which comprises:
  (a) providing a holding member having a longitudinal axis with a holding portion of the holding member having a proximal end, which is rotated by a rotating means on a dental handpiece, and a distal end; and
  (b) molding the prophylactic cup on a head portion of the holding member with the head portion mounted on the distal end of the holding portion, opposite the proximal end, wherein the head portion has a first end adjacent to the holding portion and an opposed second end along the longitudinal axis and a sidewall along and around the longitudinal axis, between the opposed ends of the head portion with at least two inlets that extend through the head portion intermediate the ends of the head portion, and wherein when the prophylactic cup is molded on the head portion, a portion of the prophylactic cup is filled in the inlets in the head portion to form an integral interlock of the prophylactic cup on the head portion of the holding member.

* * * * *